US011085921B2

(12) United States Patent
Livache et al.

(10) Patent No.: US 11,085,921 B2
(45) Date of Patent: Aug. 10, 2021

(54) ELECTRONIC NOSE OR TONGUE SENSORS

(71) Applicants: Commissariat a l'Energie Atomique et aux Energies Alternatives, Paris (FR); Centre National de la Recherche Scientifique, Paris (FR); Universite Paris-Sud, Orsay (FR)

(72) Inventors: Thierry Livache, Jarrie (FR); Arnaud Buhot, Saint Etienne de Crossey (FR); David Bonnaffe, Paris (FR); Yanxia Hou-Broutin, Bilieu (FR)

(73) Assignees: Commissariat a l'Energie Atomique et aux Energies Alternatives, Paris (FR); Centre National de la Recherche Scientifique, Paris (FR); Universite Paris-Sud, Orsay (FR)

( * ) Notice: Subject to any disclaimer, the term of this patent is extended or adjusted under 35 U.S.C. 154(b) by 638 days.

(21) Appl. No.: 14/380,288

(22) PCT Filed: Feb. 21, 2013

(86) PCT No.: PCT/IB2013/051421
§ 371 (c)(1),
(2) Date: Aug. 21, 2014

(87) PCT Pub. No.: WO2013/124810
PCT Pub. Date: Aug. 29, 2013

(65) Prior Publication Data

US 2015/0037909 A1 Feb. 5, 2015

(30) Foreign Application Priority Data

Feb. 21, 2012 (FR) ...................................... 1251579

(51) Int. Cl.
*G01N 33/543* (2006.01)
*G01N 33/00* (2006.01)

(52) U.S. Cl.
CPC ....... *G01N 33/543* (2013.01); *G01N 33/0031* (2013.01); *G01N 33/54373* (2013.01); *B01J 2219/00533* (2013.01); *B01J 2219/00596* (2013.01); *B01J 2219/00605* (2013.01); *B01J 2219/00659* (2013.01); *B01J 2219/00702* (2013.01)

(58) Field of Classification Search
None
See application file for complete search history.

(56) References Cited

U.S. PATENT DOCUMENTS 5,922,534 A * 7/1999 Lichtenwalter ...... B01J 19/0046 422/504
6,503,452 B1 1/2003 Boxer et al.
6,730,201 B1 5/2004 Kuhlman et al.
7,155,934 B2 1/2007 Lauten-Schlaeger et al.
2002/0034737 A1* 3/2002 Drmanac ............. C12Q 1/6837 435/6.12
2002/0076804 A1 6/2002 Sheppard, Jr. et al.
2003/0008413 A1* 1/2003 Kim ................. G01N 33/54353 506/32
2005/0016276 A1* 1/2005 Guan .................. G01N 29/022 73/579
2005/0233459 A1 10/2005 Melker et al.
2005/0239132 A1* 10/2005 Klapproth ........ G01N 33/54373 435/7.1
2005/0255491 A1* 11/2005 Lee .......................... B82Y 5/00 435/6.18
2008/0139406 A1* 6/2008 Hiller ................. G01N 33/6854 506/18
2009/0104630 A1* 4/2009 Reiter .................. G01N 33/558 435/7.21
2010/0222224 A1 9/2010 Suni et al.

FOREIGN PATENT DOCUMENTS

EP 0878711 A1 11/1998
JP H08-180277 A 7/1996
KR 10-0968334 A 7/2010
KR 10-2011-0108661 A 10/2011
WO 2002/012546 A2 2/2002
WO 2003/045862 A2 6/2003
WO 2005/118870 A2 12/2005
WO 2009/033370 A1 3/2009

OTHER PUBLICATIONS

International Search Report issued in corresponding International Patent Application No. PCT/IB2013/051421 dated Jun. 6, 2013.
Tang et al., "An Electronic-Nose Sensor Node Based on a Polymer-Coated Surface Acoustic Wave Array for Wireless Sensor Network Applications," Sensors, 11: 4609-4621 (2011).
Alizadeh et al., "Electronic nose based on the polymer coated SAW sensors array for the warfare agent simulants classification," Sensors and Actuators B, 129: 412-423 (2008).

* cited by examiner

*Primary Examiner* — Ellen J Marcsisin
(74) *Attorney, Agent, or Firm* — Morgan, Lewis & Bockius LLP

(57) ABSTRACT

The present invention relates to a sensor for an electronic tongue or nose for analysing a sample or detecting a target. The sensor comprises a support, on one surface of which a plurality of sensitive areas are located, each sensitive area comprising at least one receptor and being capable of transmitting a measurable signal generated by the interaction of at least one constituent of the sample or one target with at least one receptor. The sensor is characterised in that it comprises at least three sensitive areas that differ from one another in terms of their respective receptor compositions, at least one of the sensitive areas comprising a mixture of at least two different receptors, while the two other sensitive areas each comprise at least one of the two receptors.

14 Claims, 6 Drawing Sheets

ELECTRONIC NOSE OR TONGUE SENSORS

FIELD OF THE INVENTION

The present invention relates to a sensor which is of use for the production of electronic noses or tongues, and to the use thereof for analyzing fluid samples, and in particular liquid or gaseous samples.

TECHNICAL BACKGROUND

Biosensors can be separated into two distinct families.

The first family involves an analysis by virtue of one or more specific interaction(S). By way of example, mention may be made of the case of glucose biosensors using an enzyme or multiparametric systems (several sensitive zones) of DNA chip or protein chip type, which recognize ligands via specific and selective binding (DNA/DNA or antigen/protein, etc). These biochips are widely used and generate relevant information via a sensitive zone composed of a single receptor.

The second family of biosensors comprises "non-specific" systems. In this case, the information generated by a single sensitive zone, bearing a single receptor, is not interpretable since the interactions between the compounds of the medium to be analyzed and the receptor are not known. Furthermore, because of the low specificity of this type of sensor, cross reactions between the various receptors may also be observed. A set of receptors which each generate a piece of information is therefore used: all this information thus generates a pattern comparable to a digital fingerprint. For the needs of the analysis, these patterns can be compared to those derived from previous learning. This similarity with respect to the processes used in nature has led to these sensors being called an "electronic nose" as regards the study of gaseous media or an "electronic tongue" for the study of liquid media.

These electronic noses or tongues are therefore composed of a set of independent sensitive zones, each bearing a coating composed of a receptor capable of interacting with the medium studied. Each sensitive zone must therefore be associated with a system for quantifying an interaction, generally by measuring the intensity of a signal generated by the interaction. In all the cases which currently exist, each sensitive zone generates a piece of information independent of that of its neighbor. Thus, a matrix of n sensitive zones will generate n independent pieces of information which will construct the interaction pattern, often represented by a histogram, the number of the sensitive zone being associated with a signal intensity value measured on said zone.

Generally, sensitive zones are fabricated in such a way that they have variable affinities, or more generally variable physicochemical properties, with respect to the media analyzed (Turner & Magan (2004) *Nature Reviews Microbiology* 2:161-166). More recently, combinatorial approaches have emerged and peptide receptors have been grafted onto the sensitive zones. This method makes it possible to easily generate a large number of different receptors (Edwards et al. (2007) *J. Am. Chem. Soc.* 129:13575-13583). Each sensitive zone contains one and just one type of peptide and the pieces of information generated remain independent. The representations are, moreover, shown in the form of point clouds.

In this type of analysis, each piece of information therefore has the same value and weighting is not easy to carry out. These sensors do not therefore provide a continuous response. As it happens, it is found that, in these electronic tongue or nose fields, the production of the objects remains complex and a defect on one of the sensitive zones remains very frequent. The response by this sensor will therefore be distorted and, if no weighting is possible (the sensitive zones are independent of one another), the pattern generated will be difficult to interpret.

Moreover, sensors of electronic nose type generating continuous signals by virtue of optical reading have been described by Di Natale et al. (2009) *Sensors & Actuators B* 142:412-7. These sensors comprise a layer of sensitive dyes covered with permeable polymers. The reaction of the dyes after diffusion of gaseous compounds to be analyzed in the polymer is then recorded using a camera. The continuity of the response is provided in this case by the properties of the diffusing layer and not by the receptors themselves. This process remains limited by the reaction capacity of the dyes in response to the gaseous compounds. The process is not therefore applicable to the analysis of complex molecules which do not diffuse through polymers. Furthermore, since the layer of sensitive dyes is trapped under a diffusion layer, namely the polymers, no direct interaction between the receptors of the sensor and the sample can take place since a polymer barrier is required for the operating of the sensor.

Sensors of electronic nose or tongue type for more general application, in particular capable of generating a continuous response, are therefore still to be provided.

DESCRIPTION OF THE INVENTION

The present invention ensues in particular from the unexpected demonstration, by the inventors, that electronic tongue or nose sensors, comprising a support on several portions, or sensitive zones, of which are attached mixtures of two different receptors, in different ratios, exhibit signal emission profiles, said signals being generated by the interaction of constituents of a sample brought into contact with the receptors of the sensor, by the various sensitive zones, which is nonlinear and sufficiently complex to be characteristic of a given compound.

The nonlinearity of the signal indicates that the amount of information obtained is greater than that which would be obtained from the sensitive zones composed of pure receptors.

Among other things, the increase in the number of sensitive zones makes it possible to aim at an essentially continuous signal emission profile, which advantageously makes it possible to detect and eliminate any defective sensitive zones.

Finally, the use of mixtures of a small number of different receptors makes it possible to generate a large number of different sensitive zones, which is economically advantageous, insofar as this limits the costs linked to the development of different receptors.

The present invention thus relates to an electronic tongue or nose sensor for analyzing a sample or detecting at least one target, comprising a support on one surface of which is a plurality of sensitive zones, each comprising at least one receptor, it being possible for each sensitive zone to emit a measurable signal generated by the interaction of at least one constituent of the sample or of at least one target with at least one receptor, characterized in that it comprises at least three sensitive zones which differ from one another by virtue of their respective receptor compositions, at least one of the sensitive zones comprising a mixture of at least two different, or non-identical, receptors, the other two sensitive zones each comprising at least one of the two receptors.

As will become clearly apparent to those skilled in the art, the sensor according to the invention is in particular of use for implementing an electronic tongue, in particular in the context of the analysis of samples of liquid media, or an electronic nose, in particular in the context of the analysis of samples of gaseous media.

Thus, the present invention also relates to the use of a sensor as defined above, for analyzing a sample.

The present invention also relates to a process for analyzing a sample, in which:

- a sensor as defined above is brought into contact with the sample;
- the signals emitted by the sensitive zones of the sensor are measured;
- the signals measured in the previous step are compared with the signals generated independently by the sensitive zones of the same sensor, or of a second similar sensor, subsequent to bringing into contact with at least one other sample;
- the sample analyzed is described.

The present invention also relates to the use of a sensor as defined above, for defining the receptor composition of a mixture of receptors for coating a three-dimensional structure intended to interact or not to interact with at least one target.

The present invention also relates to a process for preparing a three-dimensional structure coated with a mixture of receptors, intended to interact or not to interact with at least one target, comprising:

- bringing the target into contact with a sensor as defined above;
- identifying a sensitive zone of the sensor emitting a signal of which the intensity is indicative of an affinity with the target, which may be strong or weak, similar to the desired affinity of the three-dimensional structure coated with a mixture of receptors for the target;
- optionally repeating these two steps for other targets if necessary;
- coating the three-dimensional structure with a mixture of receptors having a receptor composition similar to that of the sensitive zone identified.

Receptor

As it is understood herein, "a receptor" is a compound, which may be of any chemical type, capable of interacting, by itself or when it is assembled with one or more other receptors within a mixture so as to form a receptor assembly, with one or more constituents of the sample or with a target. As it is understood herein, a receptor may also be denoted "element or determinant for recognition or binding with one or more constituents of the sample or with a target".

Preferably, the receptors according to the invention differ from one another according to at least one physicochemical characteristic, such as, on the one hand, the hydrophilicity or the hydrophobicity and, on the other hand, the electron density, the polarity or the charge. Moreover, other conformation or configuration characteristics may differentiate them: thus, the receptors may differ from one another according to the presence of secondary structures, such as helices or sheets, or else be in stereoisomeric relationships with one another.

Thus, from a structural point of view, the receptors according to the invention may be:

- simple molecules, in particular of 1000 Da or less, such as ions, metal complexes, organic compounds, in particular organometallic compounds, amino acids, peptides, monosaccharides, oligosaccharides, nucleotides or oligo-nucleotides; or
- complex molecules, in particular of more than 1000 Da, such as polypeptides or proteins, which are optionally glycosylated, polysaccharides, lipids, DNAs, RNAs or organic polymers.

The receptors according to the invention can also constitute molecular "bricks", the assembly of which within a mixture, in particular of combinatorial type, results in a molecular construct which interacts with one or more constituents of the sample or with a target. Assemblies of receptors of this type are in particular described in Ojeda et al. (2007) *Carbohydrate Research* 342:448-459; Di Giancenzo et al. (2010) *Bioorganic & Medicinal Chemistry Letters* 20:2718-2721; Bresee et al. (2010) *Chem. Commun.* 46:7516-7518; Bresee et al. (2011) *Small* 7:2027-2031; or else Wolfenden & Cloninger, (2006) *Bioconjugate Chem.* 17:958-966.

Preferably, the receptors according to the invention have a size of less than 1 000 000 Da.

As it is understood herein, the receptors according to the invention may be independent of one another or else be connected to one another by molecular bonds, in particular covalent bonds. When the receptors are connected to one another, their association can form a macromolecule which exhibits various sites of interaction with the constituents of the sample, these sites corresponding to the receptors according to the invention.

Sensitive Zone

A "sensitive zone" according to the invention is a portion of the support capable of emitting a signal generated by the interaction between one or more constituents of the sample with the receptors that it comprises.

Such a sensitive zone occupies an area or a volume on the support which may be of variable topology and variable shape. Thus, it may be planar or in relief, i.e. the receptors are attached directly to the support or occupy a volume located above the surface by thus being distributed in the three dimensions. Moreover, the sensitive zone according to the invention may adopt any shape, it may in particular be circular or polygonal, in particular parallelepipedal. The sensitive zone according to the invention may also be separated from or joined to at least one other sensitive zone. Preferably, all of the sensitive zones of a sensor have the same area, the same topology and the same shape. Particularly preferably, the sensitive zones according to the invention have a planar topology and a circular shape. Also preferably, the area of a sensitive zone according to the invention is approximately 0.25 $\mu m^2$ to 10 $mm^2$. In addition, the thickness of the sensitive zone will preferably be between 0.5 nm and 100 μm.

The bringing into contact of a sample with a sensor according to the invention causes the emission of several measurable signals, at least one signal for each of the sensitive zones, thus forming a signal profile, which is characteristic of the sample. As those skilled in the art will clearly understand, increasing the number of sensitive zones therefore makes it possible to increase the resolution of the measurable signal profiles.

Thus, preferably, the sensor according to the invention may comprise at least 3, 4, 5, 6, 7, 8, 9, 10, 15, 20, 25, 50, 100, 500, 1000, 10 000, 100 000 or 1 000 000 sensitive zones according to the invention. Also preferably, the sensor according to the invention may comprise less than 10 000

000, 1 000 000, 100 000, 10 000, 5000, 1000, 500, 100, 50 or 25 sensitive zones according to the invention.

The surface density of the receptors makes it possible to modulate the intensity of the measurable signal.

The surface density of a receptor within a sensitive zone is given by the number of receptors included in a sensitive zone related to the area that this same sensitive zone occupies on the support. When several non-identical receptors are present in a sensitive zone, it is possible to define the respective surface densities of each of the non-identical receptors and also the surface density of the set of receptors. The surface density of a receptor may be uniform in the whole of the sensitive zone or may be variable. When it is variable, the receptors may be distributed according to surface density gradients, for example as a function of directions in the plane defined by the surface of the support. Preferably, the surface density of the set of receptors within a sensitive zone is between $10^8$ and $10^{15}$ receptors/mm$^2$. Preferably, all of the sensitive zones of the sensor have surface densities of the set of receptors that they comprise which are uniform and essentially similar.

Moreover, increasing the number of non-identical sensitive zones makes it possible to also increase the sensitivity of the sensor by multiplying the possible interactions between the constituents of the sample and the sensitive zones; this also makes it possible to increase the diversity of the signal profiles, and therefore to characterize a larger number of different constituents within the sample to be analyzed. In addition, increasing the number of non-identical sensitive zones makes it possible to increase the continuity of the profile of signals emitted by the sensitive zones of the sensor, which makes it possible to pinpoint and eliminate the defective sensitive zones generating irrelevant pieces of information.

Preferably, the sensor according to the invention comprises at least 2, 3, 4, 5, 6, 7, 8, 9, 10, 15, 20, 25, 50 or 100 different or non-identical receptors, which can also be described as different types of receptors or as receptors of different nature. Also preferably, the sensor according to the invention comprises at most 1000, 100, 50, 25 or 10 different or non-identical receptors. The same sensitive zone according to the invention may comprise a single receptor or between 2 and 20 different or non-identical receptors.

As those skilled in the art will clearly understand, each receptor, or type of receptor, is preferably present as several copies in a sensitive zone according to the invention. Thus, by way of example, when a sensitive zone is said to comprise two different receptors, it preferably comprises several copies of each of the different receptors, in particular with the surface densities previously defined. Likewise, when it is indicated that a sensitive zone comprises only one type of receptor, this means that it may comprise several copies of a single receptor or type of receptor.

Preferably, in the sensor according to the invention, at least one of the sensitive zones comprises at least 3, 4, 5, 6, 7, 8, 9 or 10 different or non-identical receptors.

Moreover, in one preferred embodiment according to the invention, a plurality of sensitive zones of the sensor, in particular at least 3, 5, 10 or 100 sensitive zones, each comprise mixtures of at least 2, 3, 4, 5, 6, 7, 8, 9 or 10 different or non-identical receptors, the different or non-identical receptors being the same in each mixture, and differ from one another in terms of the respective proportions of the different or non-identical receptors that they comprise. In other words, the sensor comprises a plurality of sensitive zones, in particular at least 3, 5, or 100, which each have different proportions of at least 2, 3, 4, 5, 6, 7, 8, 9 or 10 non-identical receptors which are present in each of the sensitive zones of the plurality of sensitive zones.

Thus, in one preferred embodiment of the invention, the sensor according to the invention comprises n non-identical receptors (n being an integer greater than one) and the sensitive zones comprise mixtures of these n non-identical receptors in variable proportions.

In the particular case where n=2, there may, for example, be 6 different sensitive zones, having surface densities of the set of receptors that they comprise which are uniform and equal to one another, with the following proportions of the two receptors A and B under consideration: A 0% B 100%; A 20% B 80%; A 40% B 60%; A 60% B 40%; A 80% B 20%; A 100% B 0%, the percentage being expressed here as the amount of the receptor under consideration in a sensitive zone relative to the total amount of receptors in the sensitive zone. The 20% serial increases in the proportion of the receptor A are called increments. In this case, the increment is constant, but it is also possible to envision non-constant increments, for example of 0, 10, 20, 30, 50, 70, 80, 90, 100% of A, made up to 100% with B.

More generally, it is possible to envision, according to the invention, k sensitive zones within which the percentage proportion of a first receptor in a mixture of two receptors changes in increments of 100/(k−1), the surface density of the set of receptors preferably being identical for each sensitive zone.

Thus, in the preferred embodiment of the invention, according to which the sensor according to the invention comprises n non-identical receptors (n being an integer greater than one), and the sensitive zones comprise mixtures of these n non-identical receptors in variable proportions, a preferred number (k) of sensitive zones to be provided for as a function of the increment i (expressed as percentage) is k=((100/i)+n−1)!/(n−1)!(100/i)!) when 100/i is an integer and n<(100/i)+1, and k=n^(100/i)/(100/i)! when n>(100/i)+1.

The decrease in the value of the increment increases the continuity and the resolution of the signal profile. In addition, this makes it possible to obtain signals which are very close to one another, or even partially redundant, and as a result to correct, or even weight, the possible defective sensitive zones. Preferably, the increment will be 50%, 33%, 20%, 10%, 5%, 4%, 3%, 2%, 1%, 0.5%, 0.4%, 0.3%, 0.2% or 0.1%.

The detection of defective sensitive zones is possible, in particular by comparison of the signals emitted by a sensitive zone of which it is desired to evaluate the functionality, with those emitted by sensitive zones which have a similar composition. Thus, in one particular embodiment of the processes according to the invention, these processes also comprise a step of verifying the functionality of the sensitive zones of the sensor, i.e. their non-defectiveness, by comparison of the signal emitted by a sensitive zone with that emitted by at least two other sensitive zones, in particular sensitive zones with a composition similar to that of which it is desired to verify the functionality. By way of example, the sensitive zones with a similar composition, for the purposes of the invention, to a sensitive zone of which it is desired to evaluate the functionality will be those in which the respective percentages of the amounts of the various receptors present per sensitive zone related to the total amount of receptors of the sensitive zone preferably differ by less than 50%, 33%, 20%, 10%, 5%, 2%, 1%, 0.5%, 0.2% or 0.1% from those of the sensitive zone of which it is desired to evaluate the functionality. Preferably, a sensitive zone 1 will be considered to be defective if the signal R1 emitted by this sensitive zone differs substantially from the signals R2 and R3 emitted by two sensitive zones with a similar composition. For example, the zone will be considered to be defective if the difference in minimum absolute value of (|R1-R2|, |R1-R3|) is at least 50, 20, 10, 5, 4, 3 or 2 times greater than the difference |R2-R3| between the two signals R2 and R3. In another example, it will be possible to use the relative difference; in this case, the sensitive zone 1 will be considered to be defective if the minimum of (2|R1−R2|/(R1+R2), 2|R1−R3|/(R1+R3)) is at least 50, 20, 10, 5, 4, 3 or 2 times greater than the relative difference 2|R2−R3|/(R2+R3). Other definitions of defective sensitive zones can be easily envisioned by those skilled in the art.

The signals obtained from sensitive zones comprising mixtures of non-identical receptors make it possible to obtain more non-redundant pieces of information on the constituents of a sample than the signals obtained from sensitive zones each comprising only identical receptors. Advantageously, this nonlinearity of the signals obtained using the sensors according to the invention can be achieved using a limited number of different receptors, which is a source of money saving.

In another preferred embodiment, the sensor according to the invention comprises at least as many sensitive zones comprising a single type of receptor as there are different receptors in the sensor, each of the different receptors of the sensor being respectively included in each of the sensitive zones comprising a single type of receptor.

The receptors are attached to the support according to the invention by any appropriate technique. Simple adsorption, electrostatic interactions or covalent grafting may, for example, be envisioned. By way of example, when the solid support is glass, it will be preferable to use receptors or receptor precursors of silane type which make it possible to carry out grafting onto the surface of the glass; when the solid support is made of gold or comprises a part made of gold, it will be preferable to use receptor precursors or receptors comprising thiol functions which will readily bond to the metal. It is also possible to immobilize the receptors in polymer matrices placed on the surface of the support.

Preferably, the attachment of the receptors to the support is carried out using receptor precursors, the structure of which does not substantially differ from the receptor (the function allowing the interaction may in particular be protected for the requirements of fabrication), or the receptors themselves, if their nature allows it.

Signal

For the purposes of the invention, the term "signal" is intended to mean a physical phenomenon. The signal is said to be measurable when it is possible to determine its presence or its absence, and/or to quantify it.

The signal according to the invention is generated following the bringing of the sample into contact with at least one sensitive zone of the sensor; its origin is the interaction between at least one receptor present within this sensitive zone and at least one constituent of the sample. The interaction generally corresponds to the formation of a bond between at least one receptor and at least one constituent of the sample, it being possible for the bond to be strong or weak and for it to be reversible. According to the invention, an emitted signal is measured for each sensitive zone as a whole. However, if necessary, in one preferred embodiment of the invention, the signals emitted by all the sensitive zones are measured.

The signal is measurable at the end point or in real time.

Preferably, the signal according to the invention is measurable in real time. The expression "real time" means that the signal is produced and measured essentially at the moment the interaction between the receptor and the constituent of the sample takes place. Advantageously, the real-time measurement of the signal provided is an additional parameter, which further increases the information provided by the sensor according to the invention by adding a temporal and nonlinear dimension to the signals.

Also preferably, the measurable signal is of mass, mechanical, acoustic, electric, or optical type. Depending on the nature of the signal according to the invention, it may in particular be measured by optical microscopy, by fluorescence microscopy, by confocal microscopy, by surface plasmon resonance, via a resonating mirror, by impedance measurement, via a quartz microbalance, via a cantilever, or by light absorption measurement.

Preferably, the sensor will make it possible to directly detect the signal. Thus, for example, when the signal is measurable by surface plasmon resonance, a suitable detection means corresponds to systems for optical reading of surface plasmon resonance. These systems are known; they generally combine a light source, for example of LED type, in order to cause a plasmon excitation, and a CCD camera to record the signal produced by the plasmon resonance. In this respect, it is quite particularly preferred that the signal according to the invention is monitored in imaging mode. As those skilled in the art are clearly aware, the imaging mode consists in monitoring the variations in signal of all the pixels constituting the image of the CCD camera used, whereas the multipoint mode itself consists in defining, or in predefining, regions of the image, i.e. a set of pixels, of which the mean of the signals obtained reflects a mean signal of the region of the image chosen.

Support

The support according to the invention consists of a material suitable for measuring the signal.

Preferably, in the sensor according to the invention, the receptors are attached to a support which transduces the signal generated by the interaction of a constituent of the medium with a sensitive zone, i.e. which relays the generated signal via a signal of another nature which is representative thereof.

When the sensor is intended for an analysis of the sample by surface plasmon resonance, the solid support is suitable for plasmon excitation and for the propagation of an evanescent wave at its surface. Advantageously, the support will be a transparent material, for example glass, covered with a metal layer, in particular of gold, in particular 10 to 100 nm thick, and more particularly 50 nm thick.

The support according to the invention may in particular consist of glass; of silicon; of organic polymer material; in particular of acrylate, PDMS, COC, PEEK or nitro-cellulose type; of metal material, in particular of silver, of gold or platinum; of carbon-based conductive material, in particular of vitreous carbon, graphite, graphene, carbon-based nanostructure, or diamond type; or a combination of at least two of these materials.

Sample

The sample according to the invention may be of any type. It is preferably a fluid and more preferably a sample of liquid medium or of gaseous medium.

It may in particular be:

a biological sample, for instance a sample of blood, of plasma, of serum, of cerebrospinal fluid, of urine, of stools, of synovial fluid, of sperm, of vaginal secretions, of oral secretions, of respiratory specimens, originating in particular from the lungs, the nose or the throat, of pus, of ascites fluid, or of specimens of cutaneous or conjunctival serous fluids;

a food sample, optionally placed in suspension, originating in particular from foods, which may be raw, cooked or prepared, from food ingredients, from spices, from ready meals, or from beverages;

a water sample, for example from water treatment or distribution plants;

a soil sample;

a gas or air sample, for instance a sample of ambient air or air from an air-conditioning system or of exhaled air.

The sample may have undergone a pretreatment. The treatment may be physical, chemical or biological; it may in particular be extraction, filtration, dilution or concentration; it may also be solubilization, milling, vaporization or suspension, in particular in the case of an initially solid sample. The treatment may also correspond to the addition of at least one signal marker to the specimen, i.e. a compound which emits an additional signal or which is capable of enabling, promoting or enhancing the production of a signal by the sensitive zones. The signal marker may bind to the constituents of the sample; it may, for example, be a fluorescent, luminescent or radioactive molecule.

The treatment may also correspond to the addition, to the sample, of an internal control, i.e. a compound of which the concentration and/or the make-up is known.

According to the use and the process as defined above, the signals emitted by the sensitive zone(s), brought into contact with the sample, are preferentially measured or recorded, in particular as a function of the contact time between the sample and the sensor according to the invention.

Target

The target according to the invention may be of any type. It can preferably be a bacterium, a eukaryotic cell, a virus, a protein, a lipid, a sugar, a nucleic acid, volatile or non-volatile organic compounds, or inorganic compounds, such as metals. From a functional point of view, the target may in particular be a medicament, a hormone, a cytokine, or else a cell receptor.

The affinity, that will here be considered synonymous with avidity, of the sensitive zone for the target is evaluated on the basis of the signal emitted by the sensitive zone. For example, when the intensity of the signal depends on the affinity of the sensitive zone for the target, a strong signal will be indicative of a strong affinity, whereas a weak signal will be indicative of a weak affinity, which constitutes the two main affinities sought.

Indeed, it will be possible to search for three-dimensional structures which have a strong affinity for at least one first target while at the same time not binding to at least one second target.

Analysis

The analysis according to the invention may in particular aim to detect and/or quantify one or more constituents of the sample. Moreover, the analysis according to the invention may also aim to describe, to categorize or to classify the samples according to two or more predefined classes, for example to classify a sample of biological origin as being healthy or malignant, or else according to the type of pathological condition, such as a cancer, that it represents, or a sample of food origin as being compliant or non-compliant. In this context, it will be possible to proceed by a comparison using control samples, which will comprise, for example, a constituent in the pure state, or which will be representative of the classes to be defined.

Thus, in one preferred embodiment of the process according to the invention:

a sensor as defined above is brought into contact with the sample;

the signals emitted by the sensitive zones of the sensor are measured;

the signals measured in the previous step are compared with the signals generated independently by the sensitive zones of the same sensor, or of a second similar sensor, subsequent to bringing into contact with at least one control sample;

the sample analyzed is described with respect to at least one control sample.

In addition, the analysis according to the invention may also aim to describe, to categorize or to classify samples according to two or more non-predefined classes. Thus, in another preferred embodiment of the process according to the invention:

a sensor as defined above, or a plurality of similar sensors as defined above, is brought into contact with a plurality of samples;

the signals emitted by the sensitive zones of the sensor(s) for each sample are measured;

the signals measured for each sample are compared with one another;

each sample is categorized with respect to all the samples analyzed.

The steps of comparison and then description defined above may require a step of supervised or nonsupervised learning. This learning can be easily carried out by those skilled in the art in the field of electronic tongues and noses, who can in particular use as a basis conventional techniques as in particular described by Jain et al. (2000) *IEEE Transactions on Pattern Analysis and Machine Intelligence* 22. 4-37. By way of example, mention may be made of principal component analysis (PCA), artificial neural networks (Turner & Magan, op. cit.), or separation by support vector machines (SVMs), in particular described by Cortes & Vapnik (1995) *Machine Learning* 20:273-297), and which has recently been successfully used for DNA chips, as is described by Brown et al. (2000) *Proc. Natl. Acad. Sci. USA* 97:262-267.

Three-Dimensional Structure

As it is understood herein, a “three-dimensional structure” according to the invention is in particular a particle, more particularly a nanoparticle, i.e. a particle having at least one nanometric dimension, in particular from 1 nm to 999 nm, or a microparticle, i.e. a particle having at least one micrometric dimension, in particular from 1 μm to 999 μm. A three-dimensional structure according to the invention may in particular be a carbon nanotube, graphene, a dendrimer, a vesicle, a micelle, a liposome, a polymer, a nanocrystal, a nanothread, magnetic particles or else porous particles. Such three-dimensional structures, which are well known to those skilled in the art, are in particular of use as a medicament, for example for binding to pathological targets.

The three-dimensional structure is coated with receptors according to the invention so as to be able to interact with at least one target. Preferably, the three-dimensional structure according to the invention is coated with a mixture of receptors, the assembly of which, in particular of combinatorial type, results in a molecular construct which interacts with the target, such as those described in Ojeda et al. (2007) *Carbohydrate Research* 342:448-459; Di Gianvincenzo et al. (2010) *Bioorganic & Medicinal Chemistry Letters* 20:2718-2721; Bresee et al. (2010) *Chem. Commun.* 46:7516-7518; Bresee et al. (2011) Small 7:2027-2031; or else Wolfenden & Cloninger, (2006) *Bioconjugate Chem.* 17:958-966.

The invention will be further explained by means of the following figures and examples, which are nonlimiting.

EXAMPLES

Example 1

Sensor of which the Sensitive Zones Consist of Mixtures of 2 Receptors

1. Fabrication of the Sensor

Two simple molecules were used as building bricks (BB) to construct a sensor comprising a support accommodating several sensitive zones combining variable proportions of receptors: lactose (BB 1) and sulfated lactose (BB 2). Nine mixtures with [BB1]/([BB1]+[BB2]) ratios of 0, 10, 20, 30, 50, 70, 80, 90 and 100% were prepared, the total concentration being constant at 20 μM. The mixtures were then deposited on a support formed by the gold surface of a prism usable for surface plasmon resonance imaging (SPRi) and were kept in contact with the surface of the prism overnight. The chip thus formed was then washed with ethanol and then dried under a stream of $N_2$.

Figure 1:
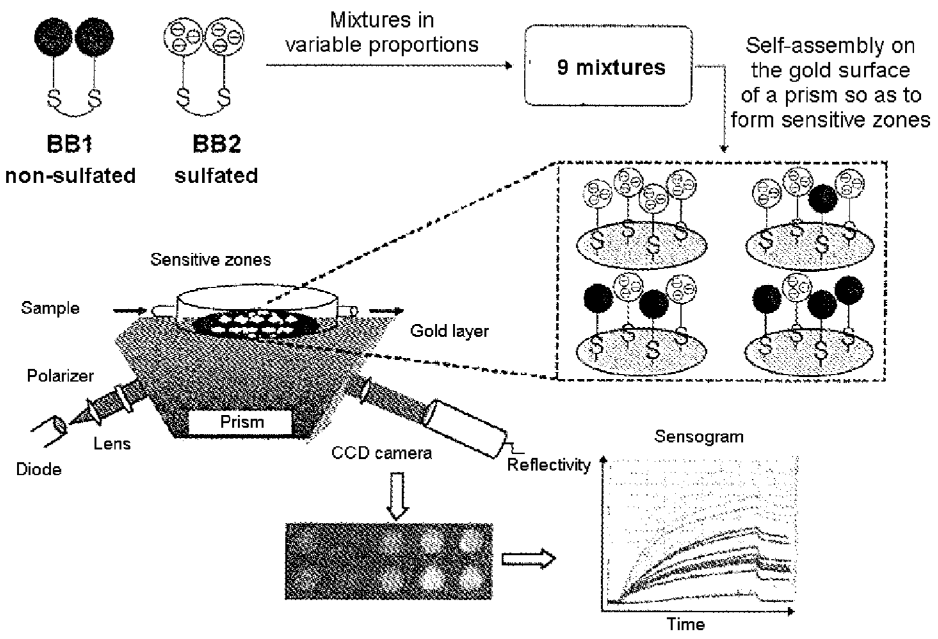
FIG. 1 describes the obtaining and the use of a sensor according to the invention. Briefly, deposits of nine mixtures of lactose (BB 1) and of sulfated lactose (BB 2) in different proportions (0, 10, 20, 30, 50, 70, 80, 90 and 100% of BB 1) are made on portions of a support consisting of a prism covered with gold so as to form sensitive zones. The sensor thus formed is placed in a cell which makes it possible to circulate various solutions to be brought into contact with the sensor. The reflectivity of the sensor is measured in the form of sensograms obtained by surface plasmon resonance imaging (SPRi) using an emitting diode and a CCD camera.

Consequently, after self-assembly, a sensor comprising nine sensitive zones, each having different proportions of BB 1 and BB 2, could be obtained, as is indicated in FIG. 1. This sensor was then used to analyze media comprising a single protein by SPRi.

2. Analysis of Control Media Containing a Single Protein

The analysis of the protein media was carried out in a 10 μl Teflon cell, connected to a degasser and to a peristaltic pump. 500 μl of protein medium were injected. The working buffer solution used comprised 10 mM HEPES, 150 mM NaCl, 0.005% Tween 20, 2 mM $MgCl_2$, pH 7.4, and was filtered and degassed before use. All the experiments were carried out at ambient temperature with a flow of 100 μl/min. Before each protein injection, bovine serum albumin was used to block the bare gold surface, in order to avoid nonspecific interactions.

Four proteins which bind to sugars were tested: the *Erythrina cristagalli* lectin (ECL), the α and γ isoforms of the CXCL12 chemokine and the pro-inflammatory cytokine interferon-γ (IFN-γ). These proteins can be classified in two groups according to their ability to bind to saccharide chains: ECL is a lectin which binds to galactose, whereas the two forms of CXCL12 and also IFN-γ bind to heparan sulfate.

Figure 2:
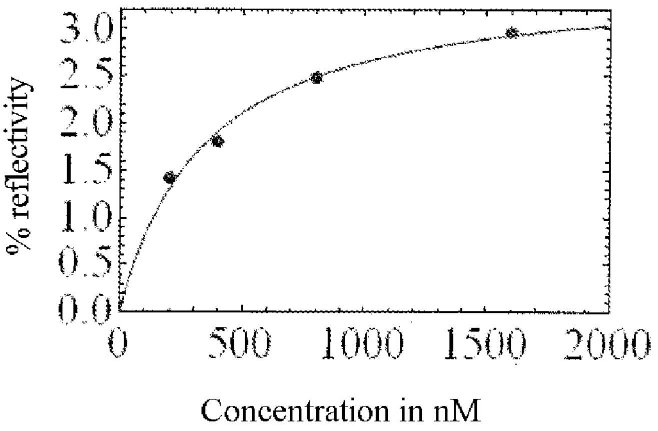
FIG. 2 represents the evolution of the reflectivity of the sensor of the invention (y-axis, as %) measured by surface plasmon resonance imaging as a function of the concentration of *Erythrina cristagalli* lectin (ECL) (x-axis, in nM) placed in the presence of the sensor.

In practice, ECL was used first to test the sensor at several concentrations (200 nM, 400 nM, 800 nM and 1.6 μM). A calibration curve (see FIG. 2) was established. This curve has a Langmuir type adsorption profile, which confirms that the system operates correctly as a sensor with a $K_D$=300+/−150 nM.

During preliminary tests, two different concentrations were used for the other proteins (100 and 200 nM for the CXCL12 isoforms, and 25 and 50 nM for the IFN-γ), in order to choose the concentrations at which the signals emitted were comparable. Finally, the concentrations that were chosen are the following: 200 nM ECL, 100 nM CXCL12-α, 100 nM CXCL12-γ and 25 nM IFN-γ. It should also be noted that, after each protein analysis, the sensor was regenerated using appropriate solutions. To this end, various solutions were tested in order to identify the solution suitable for each protein. Solutions at 0.02 M NaOH for ECL, 1 M NaCl for CXCL12-α and 1% SDS for CXCL12-γ and IFN-γ were thus retained since they allow complete regeneration of the sensor without causing damage.

The pure proteins at the selected concentrations were successively injected onto the sensors, the deposits of mixtures on the support of the sensor then lighting up at various levels of gray. These images were recorded and then converted into series of sensograms.

Figure 3:
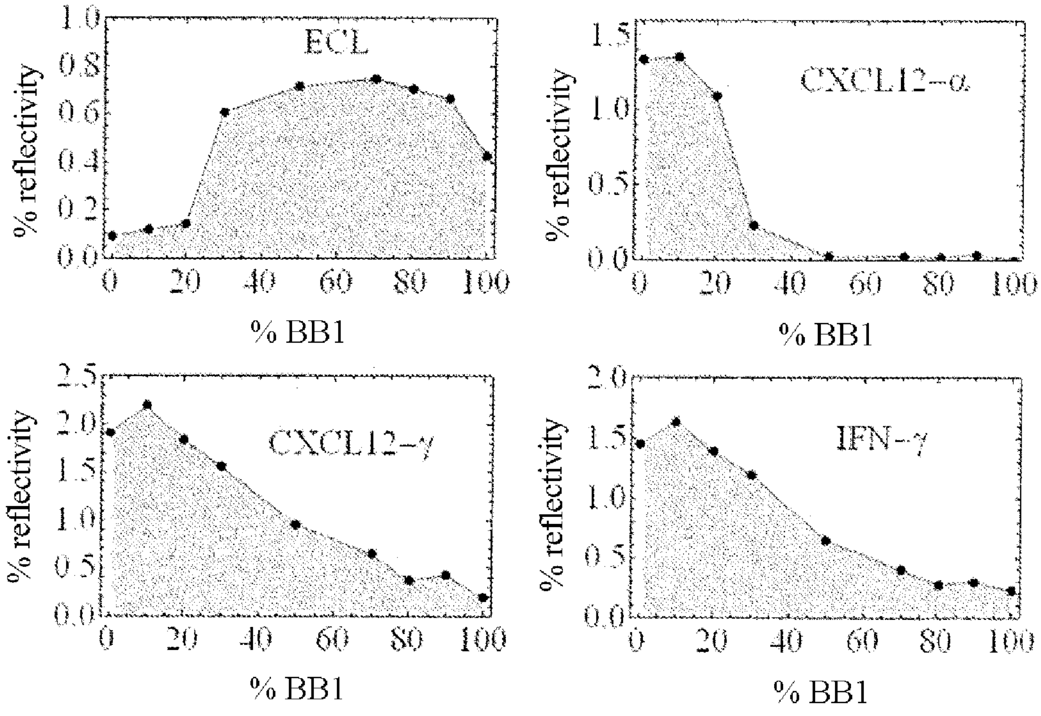
FIG. 3 represents the various continuous evolution profiles obtained respectively for ECL (200 nM), CXCL12-α (100 nM), CXCL12-γ (100 nM) and IFN-γ (25 nM) with the sensor of the invention. These profiles represent the reflectivity (x-axis, as %) as a function of the proportion of BB 1 contained in the portions of support described in FIG. 1.

Surprisingly, the inventors observed that, for a given protein, the reflectivity was dependent on the BB composition of the sensitive zones, as is visible in FIG. 3. It is in particular observed that the response of the various BB mixtures is not the simple linear addition of the response of the pure receptors. This nonlinear behavior therefore justifies, a posteriori, the use of various sensitive zones with variable proportions of each of the receptors, since the response of each sensitive zone bears an additional piece of information. Furthermore, it is observed that, for a given sensitive zone, the intensity of the response depends on the protein injected, which indicates that the sensor responds differently to each protein.

In order to illustrate the individual behavior of each protein, the reflectivity values measured one minute before the end of the protein injection were represented as a function of the proportion of BB 1 in the mixtures (FIG. 3). Interestingly, a distinctive profile in the form of a continuous evolution profile could be interpolated for each protein. The inventors were able to demonstrate that, for a given protein, the profile was essentially maintained regardless of the concentration of the protein, the intensity of the signal being, for its part, of course variable as a function of the concentration.

Consequently, such sensors could be used not only for differentiating and identifying proteins, but also for quantification purposes. Furthermore, the continuous behavior of the response of these sensors to a protein provides a significant and important advantage compared with the sets of data obtained with the conventional electronic nose and tongue sensors. This is because, since, for each of the continuous evolution profiles, the signals of one receptor correlate with the others, the abnormal signals can be excluded, thereby making it possible to carry out more precise and more correct analyte identifications.

In a detailed manner, the ECL profile, with a maximum signal at 70% of BB 1, is completely different than the others with maximum signals at 10% of BB 1, indicating that, as expected, ECL has a greater affinity for the sensitive zones of a support that are rich in lactose. Conversely, the proteins which bind to heparan sulfate have a greater affinity for the sensitive zones rich in sulfated lactose BB 2. Consequently, ECL can be easily distinguished from the others. More advantageously, the α isoform of CXCL12 gives a continuous evolution profile which is relatively different than those obtained for CXCL12-γ or IFN-γ. Indeed, for CXCL12-α, the reflectivity is virtually zero when the proportion of BB 1 is 50% or more, whereas, for CXCL12-γ or IFN-γ, it is much higher. A more thorough analysis of the continuous evolution profile represented in FIG. 3 reveals that, at the same concentration, CXCL12-γ has a much higher affinity for the sensitive zones than CXCL12-α. Thus, whereas with CXCL12-α at 100 nM no sensitive zone of the sensor exhibits a reflectivity greater than 1.35%, a signal of 2.30% is achieved with CXCL12-γ.

While it is easy to understand that ECL can be distinguished from the other proteins using the sensor, it should be noted that the two isoforms of CXCL12, which are identical in their regions 1-68, are distinguished better than CXCL12-γ with respect to IFN-γ.

However, with this first generation of sensor comprising 9 sensitive zones having different proportions of 2 receptors, it is not possible to distinguish CXCL12-γ and IFN-γ despite the difference in signal intensity. In this regard, the inventors predict that sensors prepared from additional receptors in order to generate greater diversity at the level of the sensitive zones should make it possible to distinguish heparan sulfate-binding proteins with similar but non-identical charge topologies.

3. Application to the Analysis of Complex Media

The main applications of the electronic nose and tongue technology lie in the testing and analysis of complex media. In order to test the effectiveness of the above sensor in medium analysis, the inventors tested it with a mixture of two proteins: ECL (200 nM) and CXCL12-α (100 nM) (mixture 1) and also food mixtures such as soya milk, cow's milk or rice milk.

Figure 4:
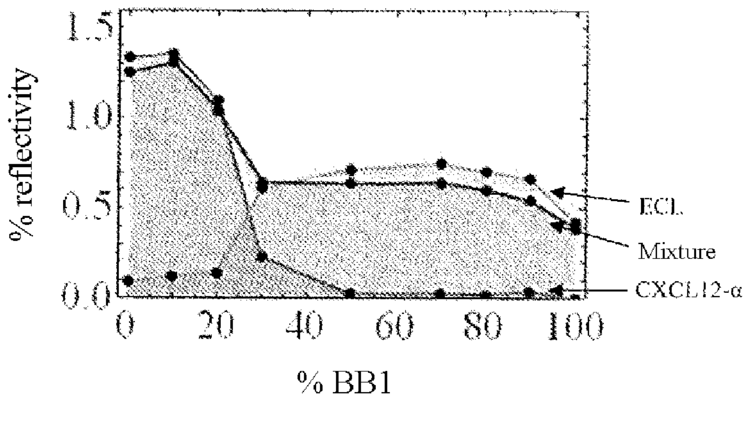
FIG. 4 represents the continuous evolution profile of an ECL+CXCL12-α mixture and those corresponding respectively to ECL and CXCL12-α alone.

The continuous evolution profile obtained is presented in FIG. 4, accompanied by the profiles obtained for the two pure proteins for comparison. This initial result demonstrates that the sensor is sensitive to the mixture and that it is capable of distinguishing the mixture from the pure proteins. In fact, it is even observed that the profile of a mixture of two proteins is close to a simple addition of the profiles of the pure proteins. This suggests that there is virtually no cooperative interaction between the proteins adsorbed on the sensitive zones of the sensor. The main advantage of this property is that it makes it possible to detect and quantify mixtures on the basis of the respective profiles of the individual components of the mixture by simple linear decomposition.

Figure 5:
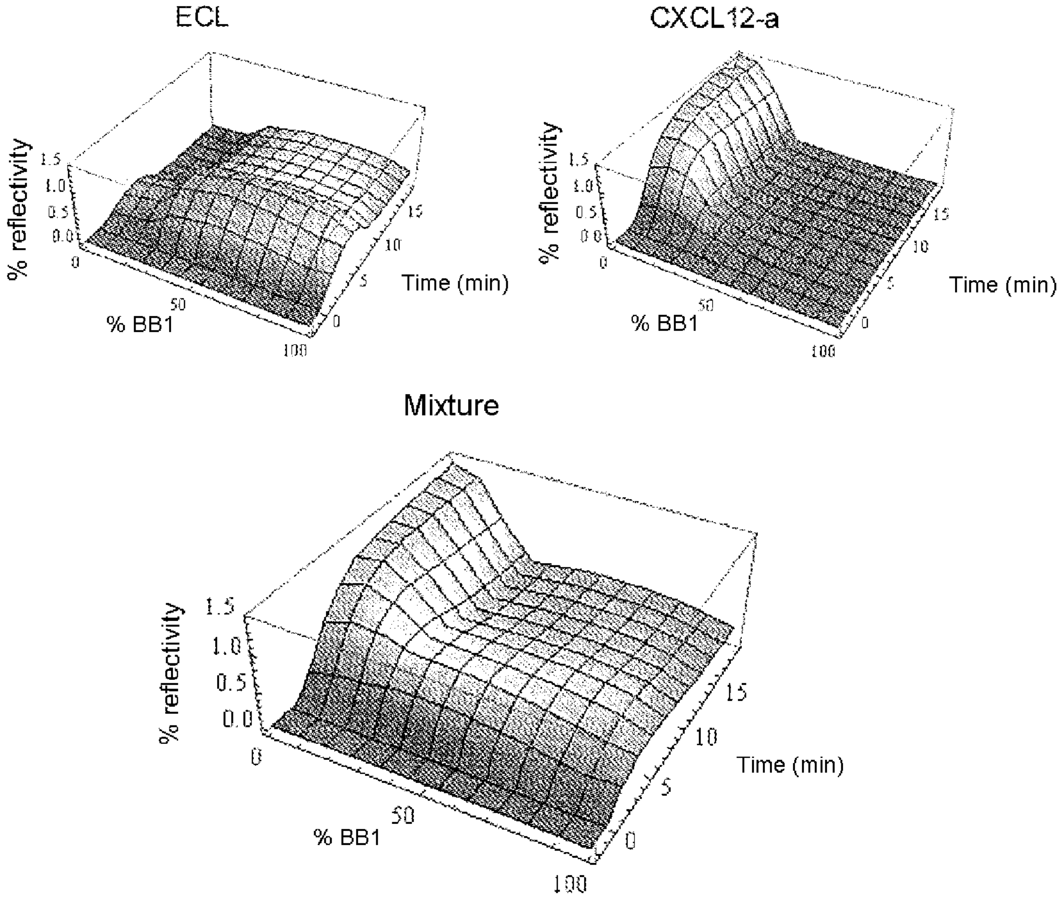
FIG. 5 represents 3D models of the continuous evolution profiles, as a function of the contact time with the sensor, obtained respectively for ECL alone (top left), for CXCL12-α alone (top right) and for an ECL+CXCL12-α mixture.

Moreover, it will be advantageous to take advantage of the real-time adsorption and desorption kinetics obtained by SPRi. This additional information could add another way to distinguish the various proteins, in addition to the continuous evolution profiles. By way of illustration, FIG. 5 presents the temporal evolution of the profile of recognition of the ECL+CXCL12-α mixture in three-dimensions.

Figure 6A:
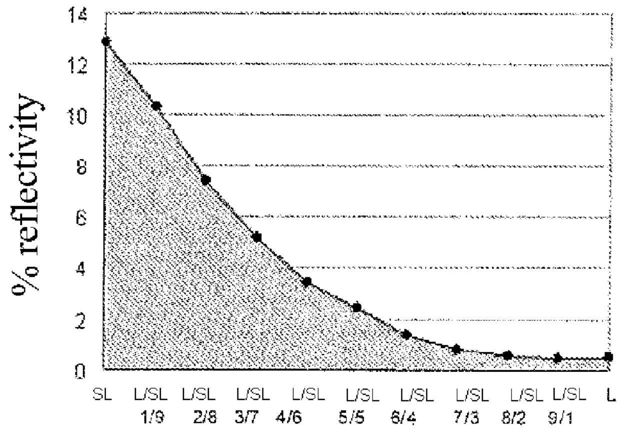
FIG. 6 represents continuous evolution profiles obtained for food mixtures: namely soya milk (FIG. 6A), cow's milk (FIG. 6B) and rice milk (FIG. 6C).
Figure 6B:
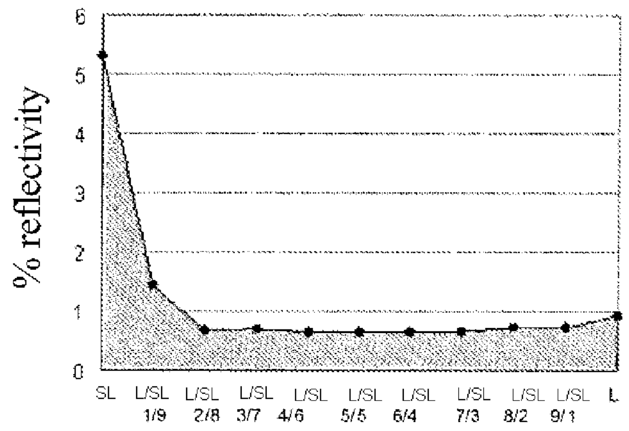
Figure 6C:
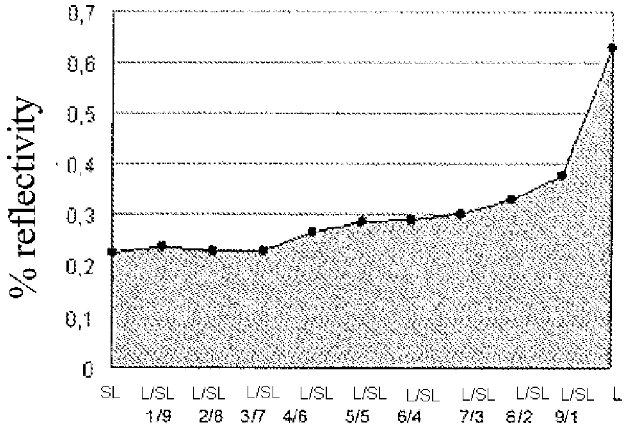

In addition, in order to make a better comparison of the response of the electronic tongue with respect to three types of food samples, soya milk, cow's milk and rice milk, a profile was produced for each sample. This profile represents the reflectivity after 6 min of rinsing as a function of the lactose/sulfated lactose (L/SL) ratios of the sensitive zones (FIG. 6). It can very easily be confirmed that, for soya milk (FIG. 6A), there is a strong affinity with several sensitive zones rich in sulfated lactose, including pure sulfated lactose, 90% SL, 80% SL, 70% SL, 60% SL and 50% SL. On the other hand, for UHT milk (FIG. 6B), there is a strong affinity only with 2 sensitive zones, pure sulfated lactose and 90% SL. This shows that the electronic tongue is capable of differentiating these two products. As regards the rice milk (FIG. 6C), the profile is completely different since the strongest affinity is obtained with the sensitive zone composed of pure lactose. These results show that the electronic tongue is effective for analyzing and differentiating complex samples. Furthermore, the profile obtained for each sample can be considered to be a signature for their identification.

Example 2

Method for Selecting Appropriate Combinatorial Surfaces

The use of decorated nanoparticles (NPs) as a therapeutic agent is a widely explored subject. Several authors have thus described systems which have a certain effectiveness.

Among the coatings used, mention may be made of: (i) specific ligands, such as antibodies for example, which will interact directly with their target, molecule to molecule, or, (ii) developed more recently, coatings composed of a small molecule (Bowman et al. (2008) *J. Am. Chem. Soc.* 130: 6896-6897; Baram-Pinto et al. (2009) *Bioconjugate Chem.* 20:1497-1502; Baram-Pinto et al. (2010) *Small* 6:1044-1050; Rele et al. (2005) *J. Am. Chem. Soc.* 127:10132-10133) or of an assembly of small molecules which in themselves individually do not have very defined biological properties (Ojeda et al. (2007) *Carbohydrate Research* 342: 448-459; Di Gianvincenzo et al. (2010) *Bioorganic & Medicinal Chemistry Letters* 20:2718-2721; Bresee et al. (2010) *Chem. Commun.* 46:7516-7518; Bresee et al. (2011) *Small* 7:2027-2031; or else Wolfenden & Cloninger, (2006) *Bioconjugate Chem.* 17:958-966), but which generate specific properties when deposited on the surface of nanoparticles.

These latter assemblies are conventionally produced combinatorially: defined sets of base bricks are mixed and then assembled with the nanoparticles. The choice of these mixtures is not necessarily rational since the appropriate structures are finally identified by screening the activity of each type of NP.

This therefore means that, in order to find active coatings on the basis of libraries of compounds not necessarily having a biological activity, it will be necessary to fabricate a large number of NPs which have coatings resulting from combinatorial mixtures. The screening of the biological activity of these NP will optionally make it possible to detect which are the active mixtures. As a result of this there is a very low ratio between the number of different NPs prepared and the number of active NPs.

In order to more successfully target these mixtures and therefore to reduce the number of nonactive NPs fabricated, it would be advantageous to be able to rapidly evaluate the activity of the mixtures of the basic bricks forming a receptor in a format more favorable to rapid high-throughput analysis.

In this context, the inventors have shown, surprisingly, that the activity of a surface composed of a mixture of receptors on a 2-dimensional (2D) support remains very similar to that of a nanoparticle coated with the same mixture.

Thus, the inventors propose to evaluate the activity of nanoparticles, or more generally three-dimensional structures, bearing at their surface a mixture of compounds forming a receptor by means of a test on a 2D sensor bearing a certain number of sensitive zones, for example in the form of spots, which are each representative of a mixture in two particular proportions of the initial compounds. The target, which may be a protein or a micro-organism for example, is then brought into contact with these sensors and the interactions are measured, by SPRi for example. The intensity of the interactions measured between the target and the various sensitive zones are indicative of the compositions of mixture to be favored for the production of the coating of the three-dimensional structures, such as NPs. Likewise, if it is preferred to avoid an interaction, a mixture composition similar to that of a sensitive zone exhibiting few or no interactions with the defined target will preferably be chosen.

The inventors therefore propose to combine with the combinatorial production of coatings of three-dimensional structures, in particular of the nanoobject or microobject type, such as NPs, dendrimers or liposomes, a 2D screening step using a sensor according to the invention, very suitable for the rapid evaluation of the surface properties. The 2D-to-3D property preservation thus makes it possible to preselect active surfaces, thereby making the development of future medicaments much faster and less expensive.

Description of the Principle:

1—A sensor is first of all constructed as indicated in Example 1 by preparing sensitive zones each consisting of a mixture with a specific proportion of the receptor-forming basic bricks, namely nine mixtures with [BB1]/([BB1]+[BB2]) ratios of 0, 10, 20, 30, 50, 70, 80, 90 and 100%, the total concentration being constant at 20 μM, BB 1 representing lactose and BB 2 representing sulfated lactose.

2—The affinity of the sensitive zones for the target, in this case interferon gamma D136 (IFNg D136) is then measured, in the present case by SPRi according to the modes of Example 1.

Figure 7:
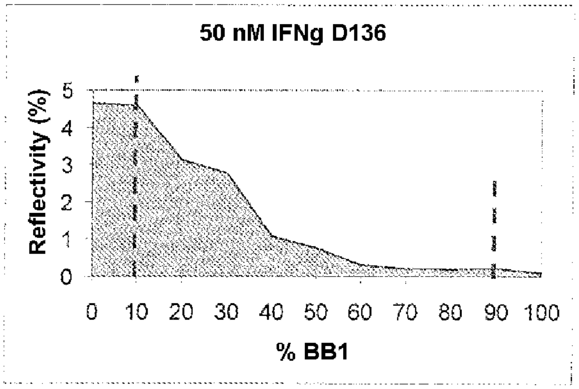
FIG. 7 represents the reflectivity measured by surface plasmon resonance imaging (y-axis, as %) for the sensitive zones of a sensor according to the invention, each representative of a mixture of lactose (BB 1) and of sulfated lactose (BB 2) in different proportions (0, 10, 20, 30, 50, 70, 80, 90 and 100% of BB 1) (x-axis) in the presence of interferon gamma D136 (IFNgD136).

3—The sensitive zone(s) offering the best affinity is (are) selected. In the present case, the relevant sensitive zone for the IFNg D136 protein consists of a 10% BB 1/90% BB 2 mixture (FIG. 7). The sensitive zone corresponding to the 90% BB1/10% BB 2 mixture was chosen as a negative control.

Figure 8:
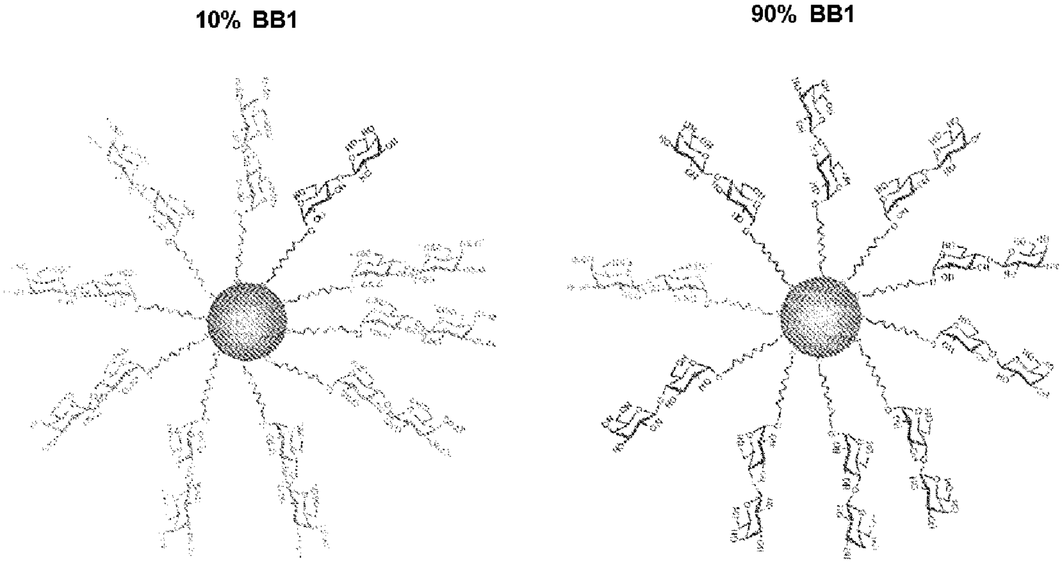
FIG. 8 represents a nanoparticle covered with a mixture of 10% BB 1/90% BB2 (on the left) and a nanoparticle covered with a mixture of 90% BB 1/10% BB2 (on the right).

4—NPs, which are gold particles coated with mixtures similar to those identified, are prepared (FIG. 8). The size of the nanoparticles is 20 nm.

Figure 9:
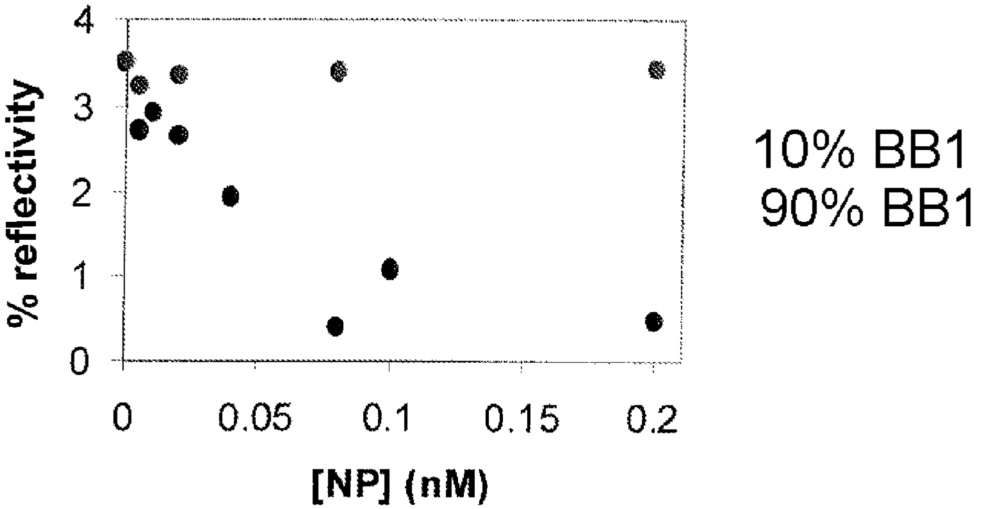
FIG. 9 represents the result of the SPRi measurement on the 10% BB 1 plot of the interaction of IFNgD136 placed in the presence of the gold nanoparticles functionalized with two types of coatings: 10% BB 1 or 90% BB 1. This effect is dependent on the nanoparticle concentration.
Figure 10:
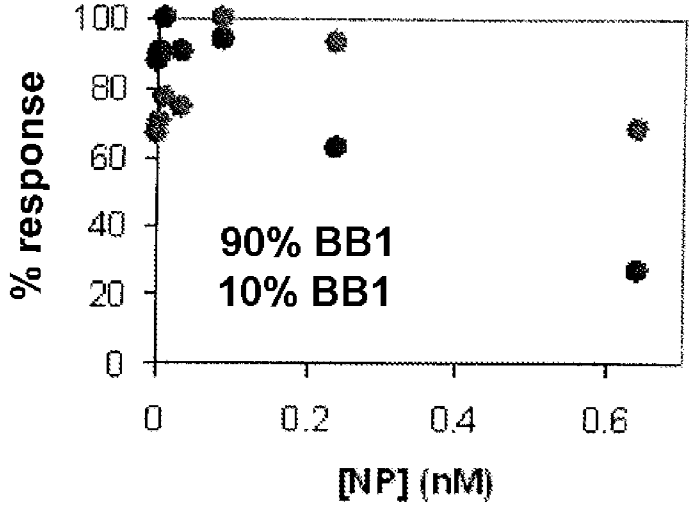
FIG. 10 represents the assaying of IFNgD136 by ELISA analysis on an anti-interferon antibody. The IFNgD136 is preincubated with gold nanoparticles functionalized with two types of coatings: 10% BB 1 or 90% BB 1. The IFNgD136 concentration of the supernatant is then evaluated by means of an ELISA assay.

5—The affinity of the NPs prepared, for the target, is verified by means of conventional biochemical tests, in this case by SPRi (FIG. 9) or by ELISA (FIG. 10).

By SPRi, it is clearly observed that the NPs with the relevant coating (10% BB1) cause a decrease in signal which is dependent on the NP concentration; on the other hand, the negative control NPs (90% BB1) do not cause any variation in signal at all.

The results of the ELISA confirm that the affinity for a target of a sensitive zone, consisting of a mixture of receptors on a 2-dimensional support, remains very similar to that of a nanoparticle coated with the same mixture.

Moreover, the same type of process, from step 1 to 5, can be carried out on several targets; for example if it is desired for the particle to bind a first target A without binding a second target B.

The invention claimed is:

1. An electronic tongue or nose sensor for analyzing a sample or detecting at least one target, comprising a support on one surface of which contains at least three sensitive zones, each comprising at least one receptor, each sensitive zone being configured to emit a measurable signal generated by the interaction of at least one constituent of the sample or of at least one target with at least one receptor;

the electronic tongue or nose sensor is characterized in that said at least three sensitive zones are different from one another by virtue of their respective receptor compositions, with at least one of the at least three sensitive zones comprising a mixture of at least two different receptors, the other two sensitive zones each comprising at least one of the at least two different receptors, wherein the electronic tongue or nose sensor has k number of sensitive zones having said at least one of the at least two different receptors, and the percentage proportion of said at least one of the at least two different receptors in the sensitive zones change in increments of 100/(k-1); and said at least three sensitive zones are different from one another in terms of the respective proportions of said at least two different receptors that said at least three sensitive zones contain.

2. The electronic tongue or nose sensor as claimed in claim 1, comprising a plurality of sensitive zones which each comprise a mixture of at least two different receptors, the different receptors being the same in each mixture.

3. The electronic tongue or nose sensor as claimed in claim 1, wherein at least one of the sensitive zones comprises a mixture of at least three different receptors.

4. The electronic tongue or nose sensor as claimed in claim 1, comprising a plurality of sensitive zones which each comprise a mixture of at least three different receptors, the different receptors being the same in each mixture, wherein said sensitive zones differ from one another in terms of the respective proportions of the different receptors that they comprise.

5. The electronic tongue or nose sensor as claimed in claim 1, comprising at least as many sensitive zones as a number of types of receptors in the sensor, each of the types of receptors in the sensor being respectively included in each of the sensitive zones.

6. The electronic tongue or nose sensor as claimed in claim 1, comprising at least one signal for each of the sensitive zones, for forming profile of the signals emitted by all the zones to identify the presence of at least one defective sensitive zone.

7. The electronic tongue or nose sensor as claimed in claim 1, wherein at least one of the other two sensitive zones comprises only one of the at least two different receptors.

8. The electronic tongue or nose sensor as claimed in claim 1, wherein said at least three sensitive zones have said at least one of the at least two different receptors at percentage proportions with a constant increment.

9. The electronic tongue or nose sensor as claimed in claim 1, wherein the at least two different receptors are not nucleotides.

10. The electronic tongue or nose sensor as claimed in claim 1, wherein the at least two different receptors are proteins.

11. An electronic tongue or nose sensor for analyzing a sample or detecting at least one target, comprising a support on one surface of which contains at least three sensitive zones and less than 10,000 sensitive zones, each comprising at least one receptor, each sensitive zone being joined to at least one other sensitive zone, wherein the at least two different receptors are protein;

the electronic tongue or nose sensor is characterized in that said at least three sensitive zones are different from one another by virtue of their respective receptor compositions, with at least one of the at least three sensitive zones comprising a mixture of at least two different receptors, the other two sensitive zones each comprising at least one of the at least two different receptors, wherein said at least three sensitive zones have said at least one of the at least two different receptors at constantly incremented percentage proportions in order, wherein the electronic tongue or nose sensor has k number of sensitive zones having said at least one of the at least two different receptors, and the percentage proportion of said at least one of the at least two different receptors in the sensitive zones change in increments of 100/(k-1); and said at least three sensitive zones are different from one another in terms of the respective proportions of said at least two different receptors that said at least three sensitive zones contain.

12. A process for analyzing a sample, in which:

the electronic tongue or nose sensor as claimed in claim 1 is brought into contact with the sample;

signals emitted by the sensitive zones of the electronic tongue or nose sensor are measured;

the signals measured in the previous step are compared with the signals generated independently by the sensitive zones of the same sensor subsequent to bringing the electronic tongue or nose sensor into contact with at least one control sample;

and the sample is analyzed with respect to at least one control sample.

13. The process as claimed in claim 12, in which:

the electronic tongue or nose sensor of claim 1 is brought into contact with a plurality of samples; the signals emitted by the sensitive zones of the sensor(s) are measured for each sample in the plurality of samples;

the signals measured for each sample in the plurality of samples are compared with one another; and each sample is categorized with respect to all the samples analyzed.

14. The process as claimed in claim 12, further comprising a step of verifying the functionality of the sensitive zones of the electronic tongue or nose sensor by comparison of the signal emitted by a sensitive zone with the signals emitted by at least two other sensitive zones.

* * * * *